US008898811B2

(12) United States Patent
Jen et al.

(10) Patent No.: US 8,898,811 B2
(45) Date of Patent: Nov. 25, 2014

(54) METAL NANOPILLARS FOR SURFACE-ENHANCED RAMAN SPECTROSCOPY (SERS) SUBSTRATE AND METHOD FOR PREPARING SAME

(71) Applicants: Yi-Jun Jen, Keelung (TW); Ching-Wei Yu, Taipei (TW)

(72) Inventors: Yi-Jun Jen, Keelung (TW); Ching-Wei Yu, Taipei (TW)

(73) Assignees: Phansco Corp., Taoyuan, Taoyuan County (TW); National Taipei University of Technology, Taipei (TW)

( * ) Notice: Subject to any disclaimer, the term of this patent is extended or adjusted under 35 U.S.C. 154(b) by 0 days.

(21) Appl. No.: 13/729,078

(22) Filed: Dec. 28, 2012

(65) Prior Publication Data
US 2013/0183540 A1 Jul. 18, 2013

(51) Int. Cl.
*G01Q 70/16* (2010.01)
*G01N 21/65* (2006.01)
*B05D 5/06* (2006.01)
*C23C 14/14* (2006.01)
*C23C 14/22* (2006.01)

(52) U.S. Cl.
CPC .............. *G01N 21/658* (2013.01); *B05D 5/061* (2013.01); *C23C 14/14* (2013.01); *C23C 14/226* (2013.01)
USPC ............... 850/58; 850/52; 356/300; 356/301; 356/326

(58) Field of Classification Search
CPC ....... G01Q 70/00; G01Q 70/08; G01Q 70/10; G01Q 70/12; G01Q 70/14; G01Q 70/16
USPC ........ 356/300, 301, 326; 850/8, 9, 52, 56, 57, 850/58, 59; 977/700, 712, 720, 742, 743, 977/846, 876
See application file for complete search history.

(56) References Cited

U.S. PATENT DOCUMENTS

2011/0245074 A1* 10/2011 Smith et al. .................. 502/309
2013/0050695 A1* 2/2013 Erickson et al. ............. 356/301

OTHER PUBLICATIONS

Chaney et al. "Aligned silver nanorod arrays produce high sensitivity surface-enhanced Raman spectroscopy substrates", Applied Physics Letters 87, 031908 (2005).*

* cited by examiner

*Primary Examiner* — Nicole Ippolito
(74) *Attorney, Agent, or Firm* — McClure, Qualey & Rodack, LLP

(57) ABSTRACT

Disclosed herein describes an SERS sensing substrate comprising upright metal nanostructures made by using oblique angle deposition (OAD) collocating with self-rotation substrate, wherein said upright nanostructures include individual upright nanopillars and metal/dielectric multilayered upright nanopillar stacks. The SERS sensing substrate exhibits higher and enhanced adsorption spectra for unpolarized incident rays in the visible and infrared wavelength regimes.

14 Claims, 11 Drawing Sheets

METAL NANOPILLARS FOR SURFACE-ENHANCED RAMAN SPECTROSCOPY (SERS) SUBSTRATE AND METHOD FOR PREPARING SAME

CROSS-REFERENCE TO RELATED APPLICATION

This utility application claims priority to Taiwan application serial number 101101168, filed on Jan. 12, 2012, that is incorporated herein by reference.

BACKGROUND OF THE DISCLOSURE

1. Field of the Disclosure

The invention relates to a surface enhanced Raman spectroscopy (SERS) sensing substrate and the manufacturing method thereof for enhancing Raman signals of specimen to be sensed.

2. Brief Description of the Related Art

Raman in 1928 invented the Raman scattering method that utilizes scattering property of light for detecting the vibrational spectroscopy signals (Raman spectroscopy) of molecule. However, the relatively minuteness of cross section of molecule beam making the detection of Raman signals difficult causes replacement of this technology by near-infrared spectroscopy (NIRS).

After the lasers were invented in the 1960, the lasers have been used as excitation source in Raman spectroscopy since 1964 for magnifying the signals. But the Raman spectroscope is still more expensive than infra-red spectroscopy limiting its application. In 1974, M. Fleischmann et al. found out that the rough metal surface can enhance significantly Raman spectroscopy signals (M. Fleischmann, P. J. Hendra, and A. J. McQulillan, "Raman spectra of pyridine adsorbed at a silver electrode" Chem. Phys. Lett. 26, 123 (1974)) and developed the surface enhanced Raman spectroscopy (SERS). This research has brought a large amount of potential applications. The surface enhanced Raman spectroscopy has improved the differentiation capability of molecule vibrational identification in the chemistry and biological system. Recent research has indicated that introducing of single molecule Raman scattering further enhances the Raman signal sensitivity. This finding has therefore extended the areas of sensor application involving surface enhanced Raman spectroscopy.

The state-of-art Raman signal instrumentation includes (a) radiation source; (b) Raman sensor; and (c) detector, wherein the Raman sensor includes surface enhanced Raman spectroscopy sensing substrate. The substrate is exposed to the radiation source and generates the localized plasmonic field, and after the localized plasmonic field is coupled to the specimen molecule being analyze, Raman photons are produced and detected by the Raman photons. Raman spectroscopy, which concerns with inelastic scattering of photons of chemical component, has been a tool for analyzing chemical substances (e.g., biological molecule) other than a tool for analyzing the molecules adsorbed by a surface.

The wide application range of surface enhanced Raman spectroscopy includes at least fast medical detection, protein research, pharmaceuticals, scientific discernment, development of biotech medicine, medical detection, health monitoring, single molecule detection, water pollution detection, agricultural products inspection, organic substance detection, environment detection, verification of carbon nano-tube. In the current measuring methods, SERS is also expected to replace the Gas chromatography and High performance liquid chromatography (HPLC).

Large area, simple vapor deposition process has attained engraving technique, such as silver zig-zag structures (Yi-Jun Jen, Ching-Wei Yu, Yu-Hsiung Wang, and Jheng-Jie Jhou, "Shape effect on the real parts of equivalent permeability of chevron thin films of silver", J. Nanophoton. 5, (2011)) and silver aligned nanorod arrays (Yi-Jun Jen, A. Lakhtakia, Ching-Wei Yu, and Chin-Te Lin, "Vapor-deposited thin films with negative real refractive index in the visible regime," Opt. Express 17, 7784 (2009)).

Since the metallic nanopillar structure's localized electric field strength can effectively enhance the Raman signals, it is proved that the silver aligned nanorod arrays (U.S. Pat. No. 7,658,991 B2) and double layers (silver nanorod/zig-zag dielectric structure) (U.S. Pat. No. 7,956,995 B2) can be applied to SERS.

SUMMARY OF THE DISCLOSURE

FIG. 1 illustrates how the upright nanopillars structure of SERS sensing substrate of this invention is produced.

FIG. 2(a), FIG. 2(b), FIG. 2(c), FIG. 2(d), FIG. 2(e), FIG. 2(f), FIG. 2(g), FIG. 2(h) respectively depicts the top view of silver nanopillars and the distribution of diameters thereof based on same deposition speed and different substrate rotation speeds.

FIG. 3(a), FIG. 3(b), FIG. 3(c), FIG. 3(d), FIG. 3(e), FIG. 3(f) respectively exemplifies single layer of nanopillar and multiple layers of nanopillar structure configuration.

FIG. 4(a), FIG. 4(b) is SEM top view showing distribution of diameters of silver nanopillar with thickness (height) of 230 nm.

Figure 8:
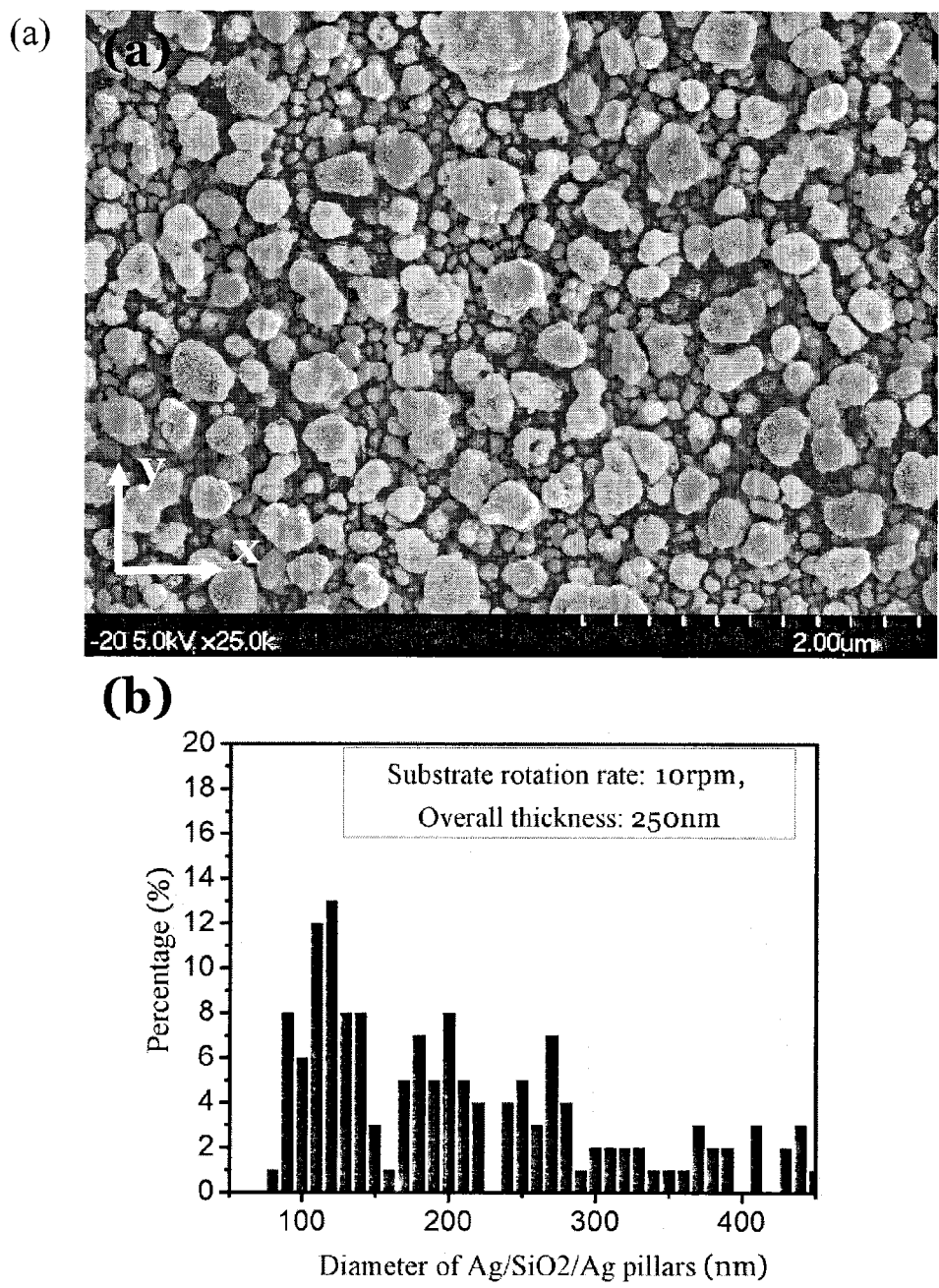

FIG. 8(a), FIG. 8(b) is SEM top view showing distribution of diameters of silver nanopillar/$SiO_2$ nanopillar/silver nanopillar multiple layers with thickness (height) of 250 nm for nanopillars.

Figure 9:
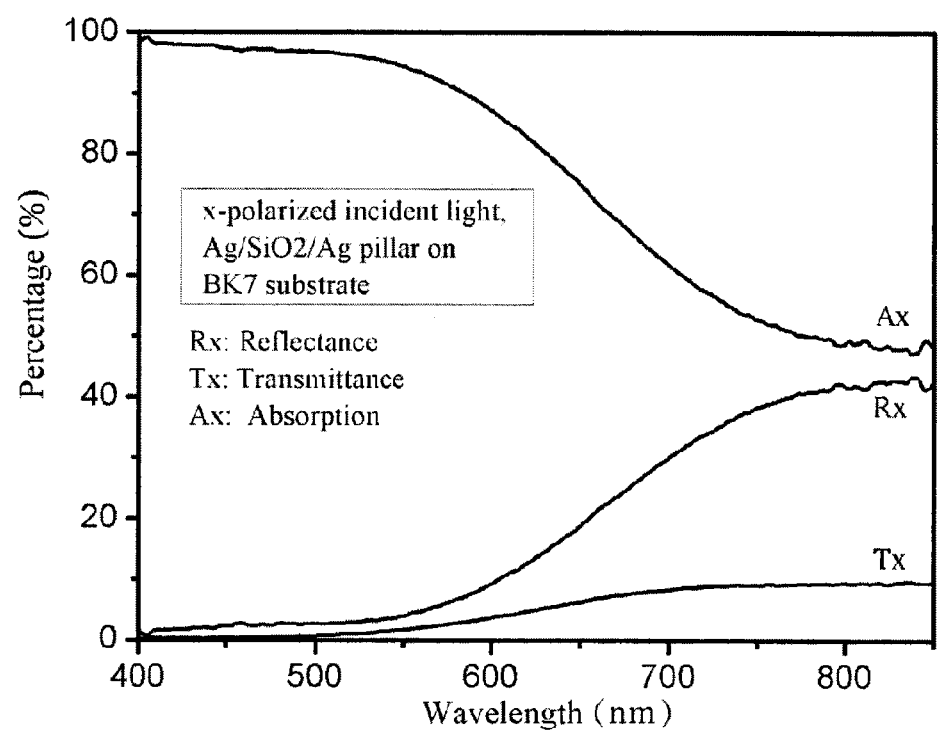

FIG. 9 shows transmisivity, reflectivity and adsorptance spectroscopy for structure in FIG. 8(a), wherein the incidence light has X polarized direction.

Figure 10:
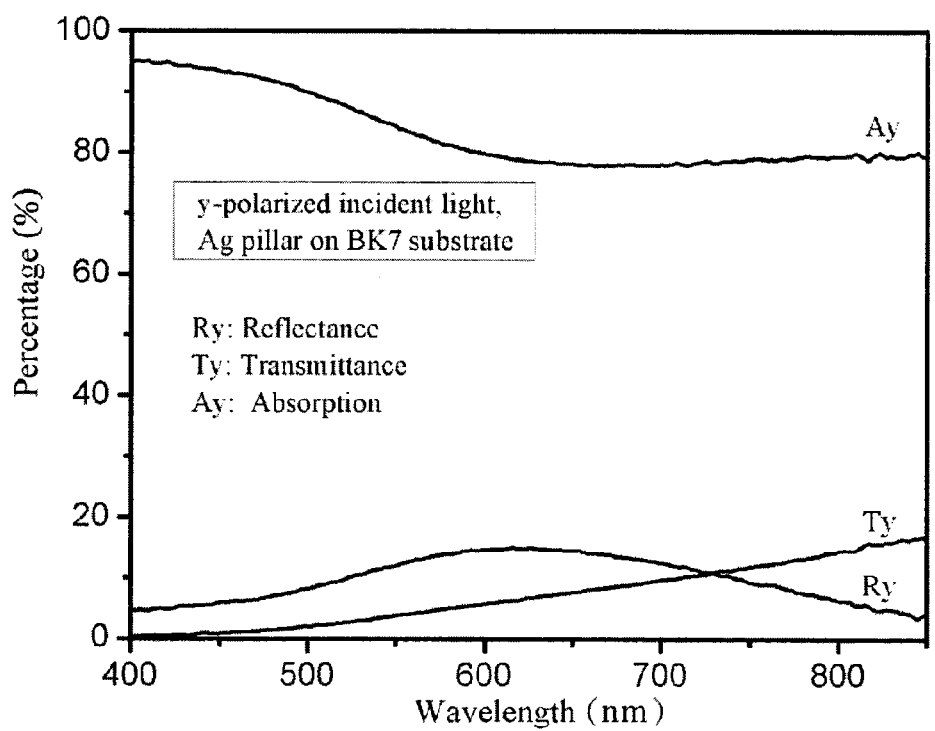

FIG. 10 shows transmisivity, reflectivity and adsorptance spectroscopy for structure in FIG. 8(a), wherein the incidence light has Y polarized direction.

Figure 11:
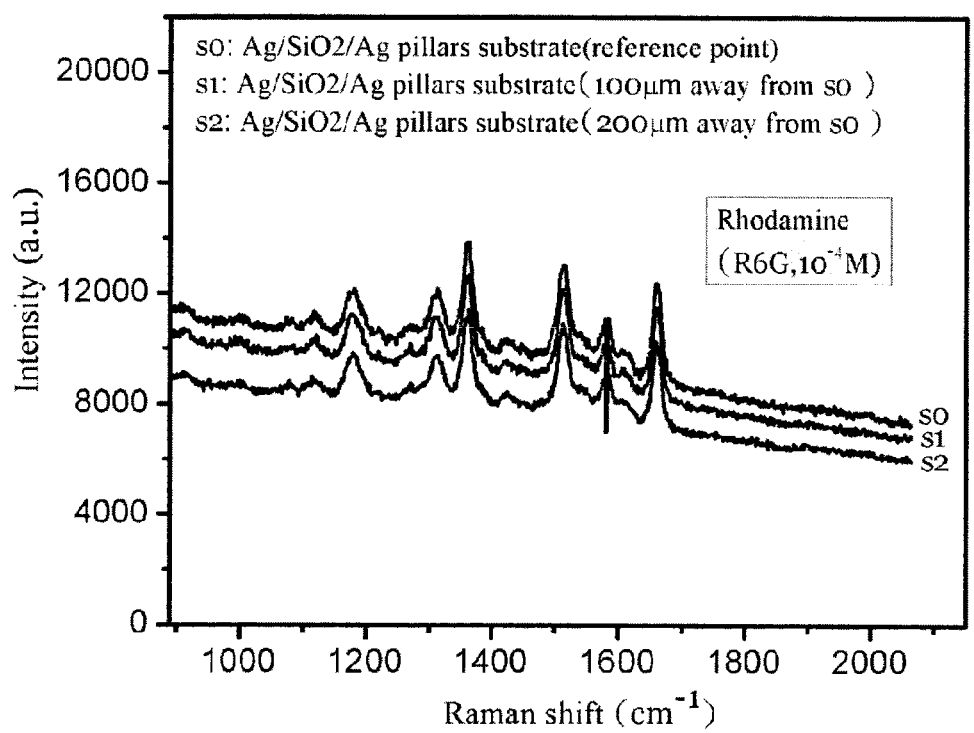

FIG. 11 shows Raman spectroscopy when using SERS substrate of silver nanopillar/$SiO_2$ nanopillar/silver nanopillar multiple layers to sense R6G of $10^{-4}$ M concentration.

While preferred embodiments are depicted in the drawings, those embodiments are illustrative and are not exhaustive, and many other equivalent embodiments may be envisioned and practiced based on the present disclosure by persons skilled in the arts.

DETAILED DESCRIPTION OF THE INVENTION

The present invention now will be described more fully herein with reference to the accompanied figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising" used in this specification do not preclude the presence or addition of one or more other selectivity features, steps, operations, elements, components, and/or groups thereof. And the term "and/or" includes any and all combinations of one or more of the associated listed items.

Unless otherwise defined, all terms used herein have the same meaning as commonly understood by one of ordinary skill in the art to which this invention belongs. It will be further understood that terms defined in commonly used dictionaries will not be interpreted in an idealized or overly formal sense unless expressly so defined herein.

To attain the objectives of the invention, the invention provides method for producing surface enhanced Raman spectroscopy (SERS) substrate having at least one metal nanopillar structure. The method first involves on the rotating substrate making metal nanopillar structure and/or dielectric nanopillar structure by oblique angle deposition technique collocating with rotating substrate. The nanopillar structure has a configuration in which the nanopillar structure is about parallel to the substrate's normal line.

Figure 1:
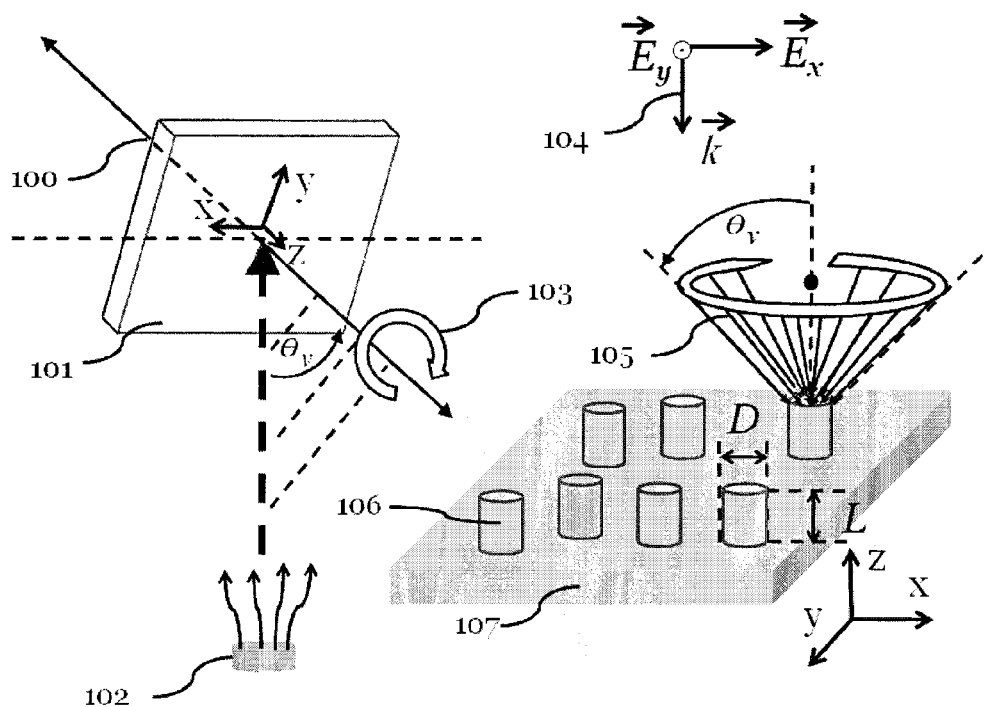

In the electron gun evaporation system, as shown in FIG. 1, the invention utilizes OAD (oblique angle deposition) collocating with rotating substrate, forming multiple silver nanopillars structure 106 of structure diameter D and height (or thickness) L on silicon wafer substrate 101 (or 107) or glass substrate 101 (or 107).

Oblique angle deposition technique is a physical vaporization deposition by which, during the formation of membrane deposition, the substrate 101 in the electron gun evaporation system is tilted by a deposition angle $\theta_v$ of substrate normal line with respect to the incoming vapor flux. In the initial deposition, the random nucleation centers are formed on the substrate and the later deposited flux causes preferential growth of nanopillars towards the direction of deposition due to the influence of shadowing effect. Incoming evaporation deposition source 102 (flux) will impinges obliquely through various different directions making nano structure, during the growing process, orients to the substrate normal line Z. And the nanopillars 106 (D, L) are then formed.

In other words, while oblique angle deposition, the substrate 101 rotates along the rotation axis 100, and the rotation direction is denoted as 103. In the meanwhile, the evaporation flux comes in along the incoming direction 105, wherein the deposition angle is $\theta v$.

In a preferred embodiment, the manufacturing parameters are (a) deposition angle is between 0~90 degree, and/or (b) deposition speed is between 0.01 nm/s~100 nm/s, and/or (c) substrate rotation speed is between 0.01 rpm~1000 rpm.

As shown in FIG. 3(a), FIG. 3(b), FIG. 3(c), FIG. 3(d), FIG. 3(e), FIG. 3(f) respectively, the nano-pillars structure configuration may be (a) metal nanopillar 301/substrate 302, or (b) metal nanopillar 303/dielectric nanopillar 304/substrate 305, or (c) metal nanopillar 308/dielectric nanopillar 307/metal nanopillar 306/substrate 309, or (d) a first metal material nanopillar 310/a second metal material nanopillar 311/substrate 312, or (e) metal nanopillar 313/dielectric nanopillar 314/metal nanopillar 315/dielectric nanopillar 316/substrate 317, or (f) metal nanopillar 318/metal nanopillar 319/periodical structures of seed layer 320/substrate 321. Or, it also can be (g) metal nanopillar/dielectric nanopillar/periodical structures of seed layer/substrate (not shown). The metal nanopillar 318, or 319 may be nanopillars of identical or distinct metal material.

The metal material is selected from a group consisting of group of material capable of enhancing Raman signals including gold (Au), silver (Ag), copper (Cu), aluminum (Al), lithium (Li), palladium (Pd), and platinum (Pt).

The nanopillars structure is made on substrate of periodical or nonperiodical structures, or periodical structures of seed layer/substrate. Therefore the substrate 101, 107, 302, 305, 309, 312, 317, 321 might be substrate which is flat or has periodical patterns.

The seed layer 320 is selected from a group consisting of dielectric or photo resist material. The substrate 101, 107, 302, 305, 309, 312, 317, 321 might be selected from a group of good adhesive property materials to metal/dielectric consisting of silicon wafer, acrylic (PMMA), glass, PET, Al2O3, PC etc.

The metal or dielectric nanopillar structure has following properties: (a) nanopillar diameter (D): 10 nm~1.5 μm, (b) distance of center to center of two adjacent nanopillars: 10 nm~1.5 μm, (c) total height of pillar: 10 nm~5 μm.

From the above recitations, it is known that a surface enhanced Raman spectroscopy (SERS) sensing substrate produced includes a substrate; at least one single layer of metal nanopillar structure formed on the substrate, the nanopillar structure has a configuration in which the nanopillar structure is about parallel to the substrate's normal line. The configurations are illustrated in FIG. 3(a), FIG. 3(b), FIG. 3(c), FIG. 3(d), FIG. 3(e), or FIG. 3(f).

The Raman instrumentation embodied by above methodology includes (a) irradiation source; (b) Raman sensor including the above mentioned sensing substrate as shown in FIG. 3(a), FIG. 3(b), FIG. 3(c), FIG. 3(d), FIG. 3(e), FIG. 3(f); and (c) detector. Wherein the Raman sensor generates localized plasmonic field after being exposed by the irradiation source, and the plasmonic field enhances Raman signals of the specimen to be sensed.

The above irradiation source might be laser devices capable of producing single mode wavelength, which includes solid state-laser, semiconductor (diode) lasers, He—Ne laser, and gas laser.

Preferred Embodiment

The FIG. 3(a) is used again for following reiterations. In an exemplified manufacturing process, the silver particles of 3 mm diameter of purity 99.999% are adopted as evaporation source 102 and the electron beam gun evaporation system is maintained at base pressure of $4\times10^{-6}$ Pa. During deposition, the substrate is rotated about the axis of substrate normal line at a constant speed. The lengths of the pillars are controlled by using a quartz thickness monitor placed next to the substrate. The deposition rate is maintained and the deposition angle is kept at $\theta_v$.

Figure 2:
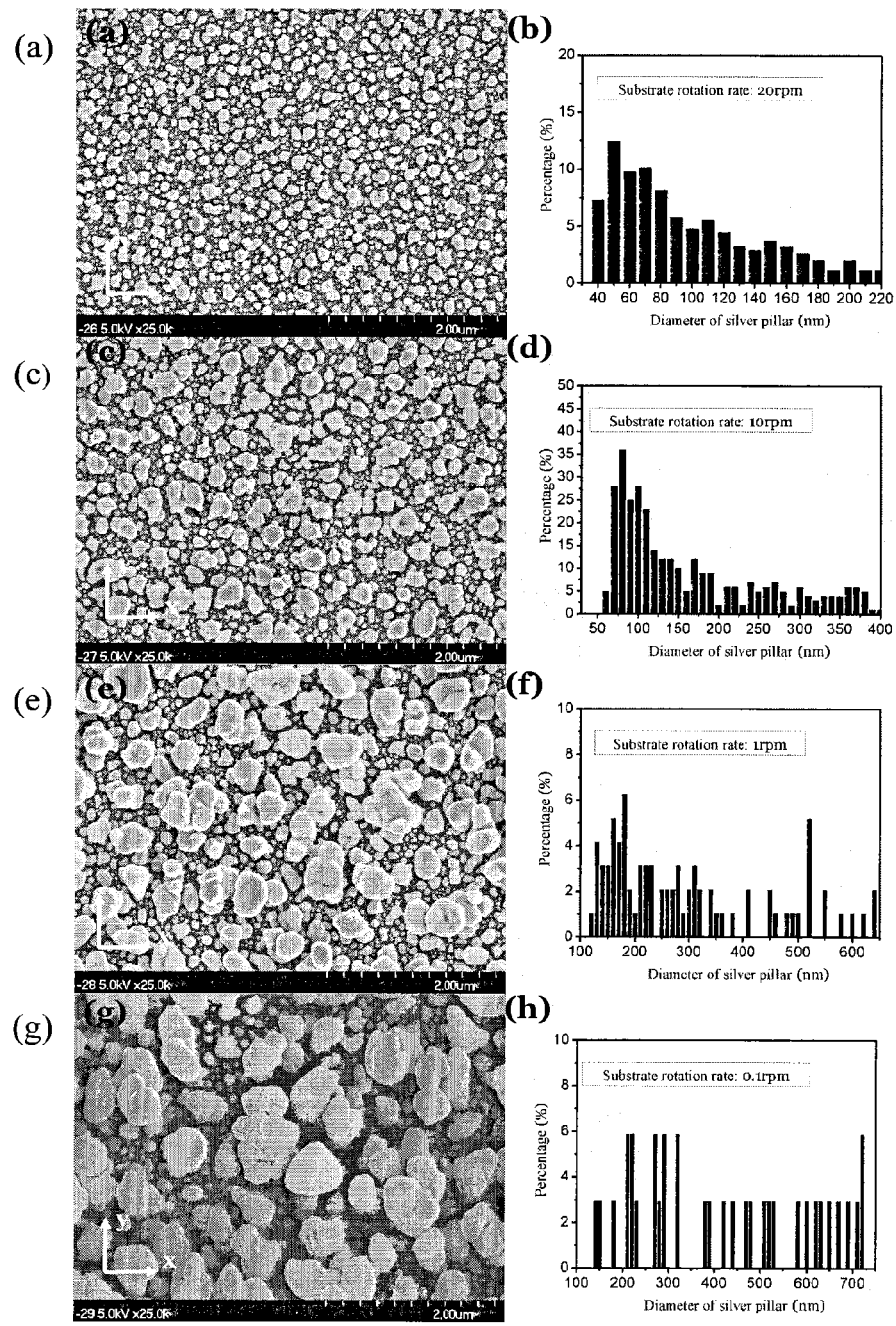

FIG. 2(a), (c), (e), (g) are respectively the top view diagrams taken by scanning electron microscope (SEM) for deposition speed=1.2 nm/s, $\theta_v$=89 degrees, collocating with four types of substrate rotation speed of 20 rpm, 10 rpm, 1 rpm and 0.1 rpm, wherein in FIG. 2(a), (c), (e) nanopillar L=120 nm, and in FIG. 2(g) the nanopillar is L=250 nm.

FIG. 2(b), (d), (f), (h) respectively shows, at deposition speed=1.2 nm/s, $\theta_v$=89 degrees collocating with four rotation speeds of substrate 20 rpm, 10 rpm, 1 rpm and 0.1 rpm, the corresponding distribution of nanopillar diameter D. From FIG. 2(b), (d), (f), it is found that while the deposition speed is unchanged, lowering of substrate rotational speed will result in the distribution of diameter D of nanopillars moving to direction of larger dimension. In addition, increase of nanopillar's height L (FIG. 2(g)) also results in larger of diameter D of nanopillar.

Figure 3:
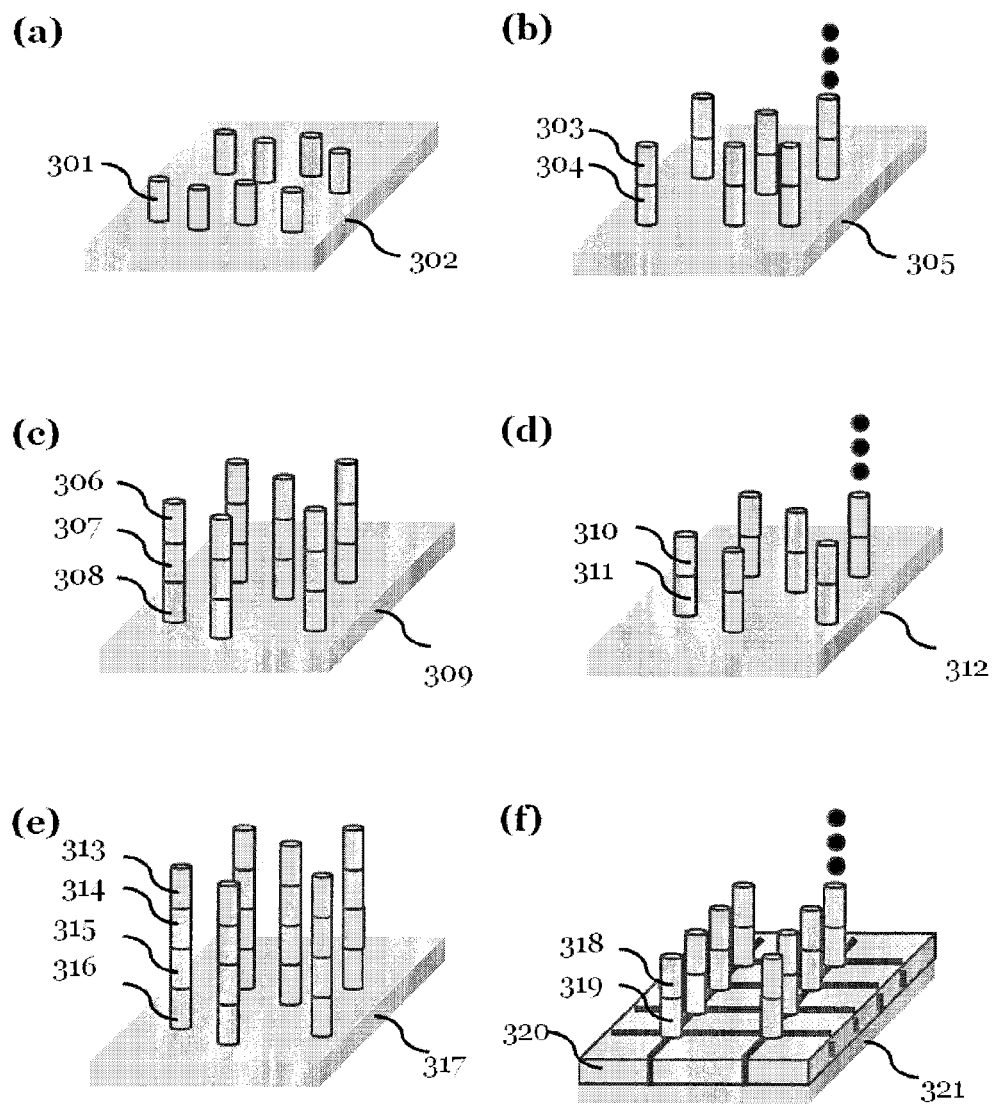

Other than single layer of metal nanopillar, pillars of different materials may be formed in a stack by same process. As shown in FIG. 3 and above recitations, the substrate 302 (or 305, 309, 312, 317, 321) might be substrate having periodical structure patterns, the dimensions of seed layer 320 and substrate of periodical structure are in nano-scale as well. Other than the substrate, this configuration may further extend to a configuration which is formed by further upward periodical stacks.

FIG. 4(a) shows the top view diagram taken by SEM on the specimen of single layer of silver nanopillars of L=230 nm obtained by process under the deposition speed 1.2 nm/s, $\theta_v$=89 degrees collocating with rotational substrate speed of 10 rpm. FIG. 4(b) shows diameter D distribution of single layer of silver nanopillars.

Figure 4:
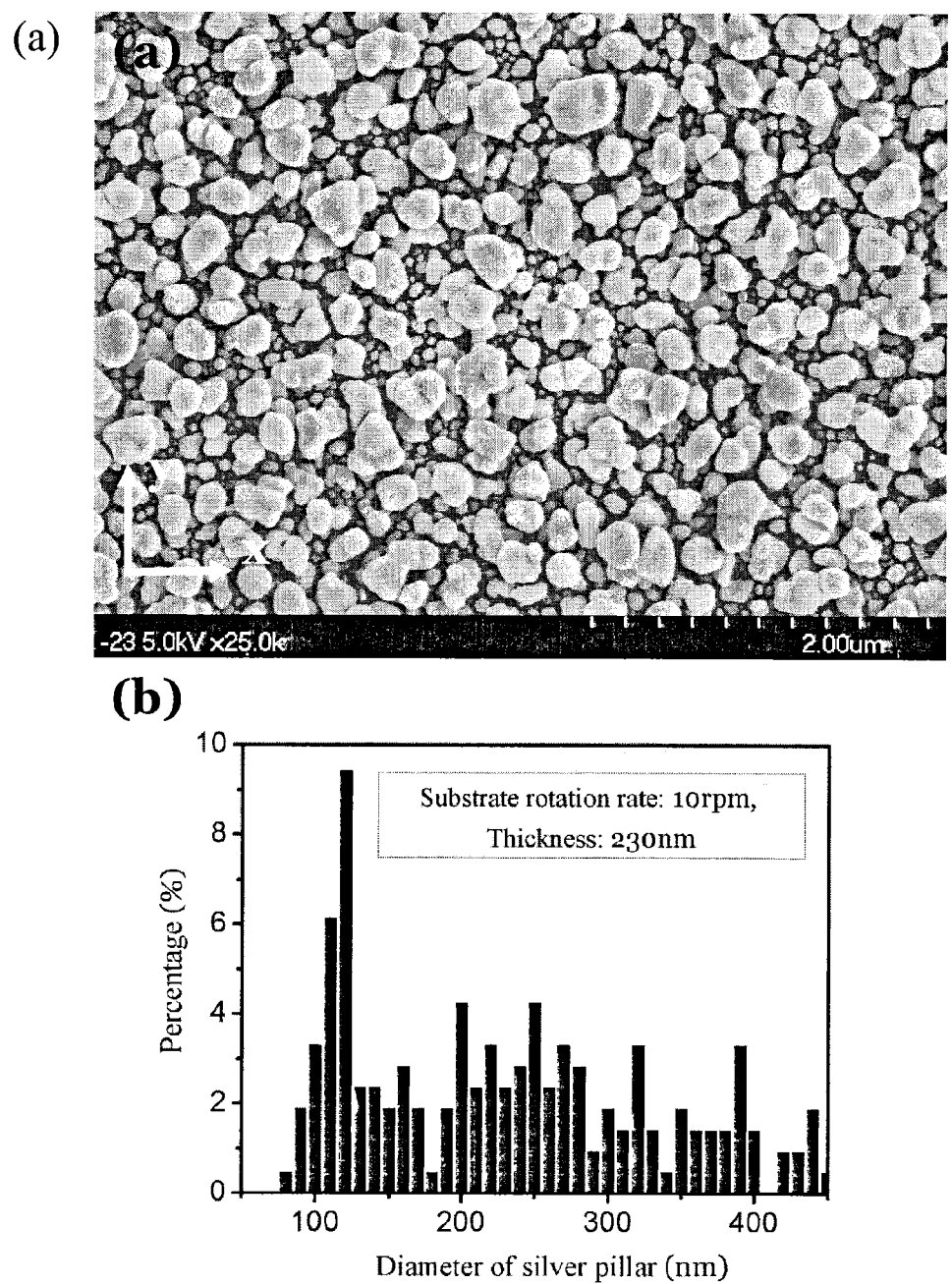
Figure 5:
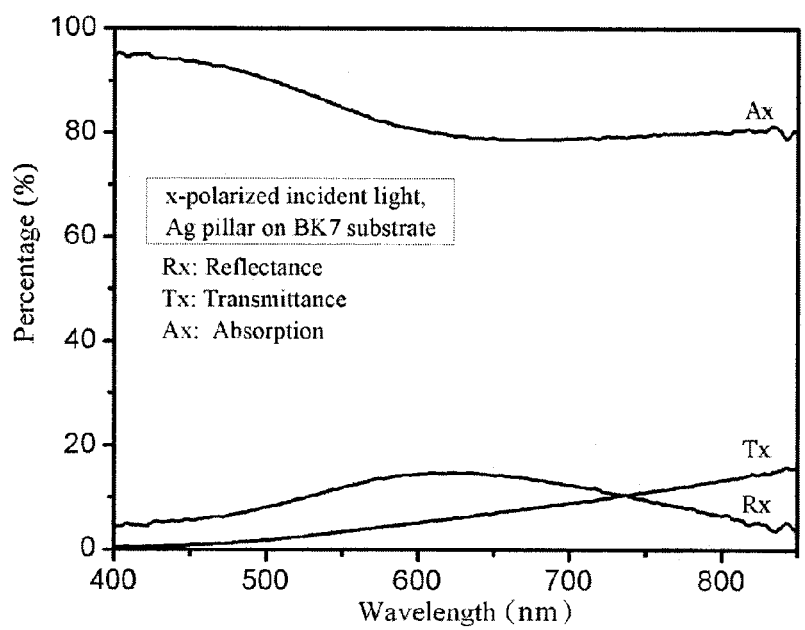
FIG. 5 shows transmisivity, reflectivity and adsorptance spectroscopy for structure in FIG. 4, wherein the incidence light has X polarized direction.
Figure 6:
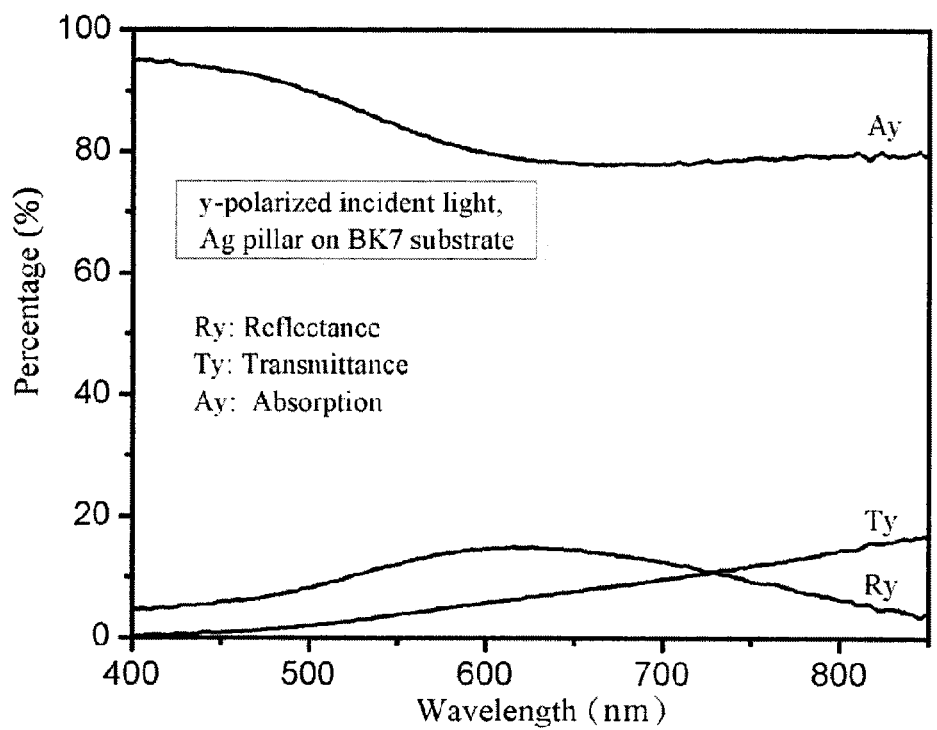
FIG. 6 shows transmisivity, reflectivity and adsorptance spectroscopy for structure in FIG. 4, wherein the incidence light has Y polarized direction.

FIG. 5 and FIG. 6 respectively shows the transmissivity (T), reflectivity (R) and adsorbtivity (A) spectroscopy for structure of FIG. 4 while x polarized incidence light and y polarized incidence light are respectively used. From FIG. 5 and FIG. 6, the spectroscopy property of this single layer of silver nanopillar structure is not correlated with polarization, wherein the adsorbtivity (A) exceeds 78% in range of 400 nm~850 nm.

Figure 7:
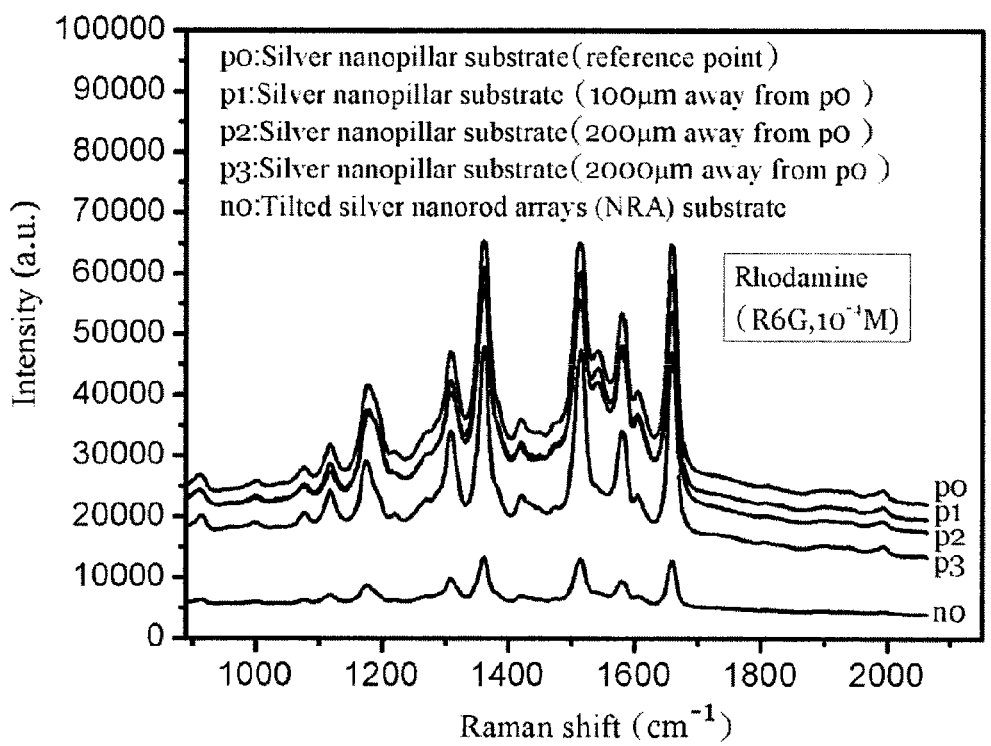
FIG. 7 shows Raman spectroscopy when using SERS substrate of single layer of silver nanopillar to sense R6G of $10^{-4}$ M concentration.

FIG. 7 shows Raman spectroscopy at different locations (p0, p1, p2, p3) of surface while configuration of FIG. 3(a) is used as SERS substrate. The 532 nm laser of 100 mW is used for the excitation light source, the measurement are made at above locations for Rhodamine (R6G) of $10^{-4}$ M concentration. In particular, the excitation light source laser has light-spot size of 1 μm over the nano structure. Rhodamine can be obtained by diluting of de-ionized water to needed $10^{-4}$ M concentration. The p0 distribution is Raman spectroscopy of reference point, the p1 distribution is Raman spectroscopy for location distant from the reference point p0 by 100 μm, the p2 distribution is Raman spectroscopy for location distant from the reference point p0 by 200 μm, the p3 distribution is Raman spectroscopy for location distant from the reference point p0 by 2000 μm. From FIG. 7, compared to Raman spectroscopy of silver aligned nanopillar arrays, it is observed that the Raman signals of the silver nanopillars shown in FIG. 3(a) configuration are stronger than that of the silver aligned arrays.

In the followings, the triple layers of metal 306/dielectric 307/metal 308/substrate 309 shown in FIG. 3 (c) is used for explaining the advantage or benefit of the invention.

FIG. 8(a) shows the top view diagram taken by SEM on the specimen of single layer of silver nanopillars of L=250 nm obtained by process under the deposition speed 1.2 nm/s, $\theta_v$=89 degrees collocating with rotational substrate speed of 10 rpm. FIG. 8(b) shows diameter D distribution of single layer of silver nanopillars.

FIG. 9 and FIG. 10 respectively shows the transmissivity (T), reflectivity (R) and adsorbtivity (A) spectroscopy for structure of FIG. 8(a) while X polarized incidence light and Y polarized incidence light are respectively used. From FIG. 9 and FIG. 10, the spectroscopy property of this single layer of silver nanopillar structure is not correlated with polarization, wherein the adsorbtivity (A) exceeds 57% in range of 400 nm~850 nm.

FIG. 11 shows Raman spectroscopy at different locations (s0, s1, s2) of surface while configuration of silver nanopillar/SiO$_2$ nanopillar/silver nanopillar multiple layers of is used as SERS substrate. The 532 nm laser of 100 mW is used for the excitation light source, the measurement are made at above locations for Rhodamine (R6G) of $10^{-4}$ M concentration. In particular, the excitation light source laser has light-spot size of 1 μm over the nano structure. Rhodamine can be obtained by diluting of de-ionized water to needed $10^{-4}$ M concentration. The p0 distribution is Raman spectroscopy of reference point, the p1 distribution is Raman spectroscopy for location distant from the reference point p0 by 100 μm, the p2 distribution is Raman spectroscopy for location distant from the reference point p0 by 200 μm. From FIG. 7, compared to Raman spectroscopy of tilting silver nanopillars array, it is observed that stronger and stable SERS signals are resulted by nanopillars structure shown in FIG. 3(c) configuration.

The scope of protection is limited solely by the claims, and such scope is intended and should be interpreted to be as broad as is consistent with the ordinary meaning of the language that is used in the claims when interpreted in light of this specification and the prosecution history that follows, and to encompass all structural and functional equivalents thereof.

What is claimed is:

1. A method for making surface enhanced Raman spectroscopy (SERS) substrate at least having metal nanopillars, comprising:
    on a rotating substrate along a normal line of the substrate, forming metal nanopillars by a oblique angle deposition process, the metal nanopillars having a configuration in which nanopillars are about parallel to the normal line of the substrate.

2. The method of claim 1, the configuration is selected from a group consisting of:
    (a) solely metal nanopillar/substrate,
    (b) metal nanopillar/dielectric nanopillar/substrate,
    (c) metal nanopillar/dielectric nanopillar/metal nanopillar/substrate,
    (d) a first metal nanopillar/a second metal nanopillar/substrate,
    (e) metal nanopillar/dielectric nanopillar/metal nanopillar/dielectric nanopillar/substrate,
    (f) metal nanopillar/metal nanopillar/periodical structures of seed layer/substrate, and
    (g) metal nanopillar/dielectric nanopillar/periodical structures of seed layer/substrate.

3. The method of claim 1, wherein the oblique angle is between 0~90 degrees, the deposition speed is between 0.01 nm/s~100 nm/s, and the substrate rotation speed is between 0.01 rpm~1000 rpm.

4. The method of claim 1, the metal nanopillar is selected from a group consisting of gold (Au), silver (Ag), copper (Cu), or aluminum (Al), lithium (Li), palladium (Pd), platinum (Pt) which is capable of enhancing Raman signals.

5. The method of claim 4, the metal nanopillars are produced on the substrate having periodical, non-periodical structures or on the substrate of periodical structures of seed layer/substrate.

6. The method of claim 2, the metal or dielectric nanopillars respectively has the following properties:
    (a) diameter of nanopillar: 10 nm~1.5 μm, (b) distance of centers between two adjacent nanopillar: 10 nm~1.5 µm, (c) total height of nanopillar: 10 nm~5 µm.

7. The method of claim 2, the seed layer is selected from a group consisting of dielectric or photo resist material, the substrate is selected from a group consisting of silicon wafer, (PMMA), (glass), PET, $Al_2O_3$, PC which has good adhesive property with the metal nanopillar/dielectric nanopillar.

8. A surface enhanced Raman spectroscopy (SERS) sensing substrate, comprising:
   a substrate;
   at least one layer of metal nanopillar structure formed one the substrate, the metal nanopillar structure has a configuration in which the metal nanopillar structure are about parallel to a normal line of the substrate.

9. The surface enhanced Raman spectroscopy sensing substrate of claim 8, the configuration is selected from a group consisting of:
   (a) solely metal nanopillar/substrate,
   (b) metal nanopillar/dielectric nanopillar/substrate,
   (c) metal nanopillar/dielectric nanopillar/metal nanopillar/substrate,
   (d) a first metal nanopillar/a second metal nanopillar/substrate,
   (e) metal nanopillar/dielectric nanopillar/metal nanopillar/dielectric nanopillar/substrate,
   (f) metal nanopillar/metal nanopillar/periodical structures of seed layer/substrate, and
   (g) metal nanopillar/dielectric nanopillar/periodical structures of seed layer/substrate.

10. A method for making a surface enhanced Raman spectroscopy (SERS) substrate having metal nanopillar selectively interleaving with dielectric nanopillar, comprising:
    on a rotational substrate along a normal line of the substrate, producing stack of multiple layers of nanopillar structure of metal nanopillar/dielectric nanopillar material by oblique angle deposition process, the substrate has a configuration in which the multiple layers of nanopillar structure of metal nanopillar/dielectric nanopillar material are about parallel to a normal line of the substrate.

11. The method of claim 10, the metal nanopillar material is selected from a group consisting of gold (Au), silver (Ag), copper (Cu), or aluminum (Al), lithium (Li), palladium (Pd), platinum (Pt), the dielectric nanopillar material is selected from a group consisting of $SiO_2$, $Ta_2O_5$, ZnS, $TiO_2$, $Al_2O_5$, $MgF_2$ which is high penetration material with good connectivity property with the metal nanopillar material.

12. The method of claim 8, the configuration is selected from a group consisting of:
    (a) solely metal nanopillar/substrate,
    (b) metal nanopillar/dielectric nanopillar/substrate,
    (c) metal nanopillar/dielectric nanopillar/metal nanopillar/substrate,
    (d) a first metal nanopillar/a second metal nanopillar/substrate,
    (e) metal nanopillar/dielectric nanopillar/metal nanopillar/dielectric nanopillar/substrate,
    (f) metal nanopillar/metal nanopillar/periodical structures of seed layer/substrate, and
    (g) metal nanopillar/dielectric nanopillar/periodical structures of seed layer/substrate.

13. A surface enhanced Raman spectroscopy (SERS) sensing substrate comprising:
    a substrate;
    a stack of multiple layers of nanopillar metal/nanopillar dielectric material, selectively interleaving with each other, formed on the substrate, the substrate has a configuration in which the multiple layers of nanopillar metal/nanopillar dielectric material are about parallel to a normal line of the substrate.

14. The surface enhanced Raman spectroscopy sensing substrate of claim 13, the configuration is selected from a group consisting of:
    (a) metal nanopillar/dielectric nanopillar/substrate,
    (b) metal nanopillar/dielectric nanopillar/metal nanopillar/substrate,
    (c) a first metal nanopillar/a second metal nanopillar/substrate,
    (d) metal nanopillar/dielectric nanopillar/metal nanopillar/dielectric nanopillar/substrate,
    (e) metal(or dielectric) nanopillar/metal(or dielectric) nanopillar/periodical structures of seed layer/substrate, and
    (f) metal nanopillar/dielectric nanopillar/periodical structures of seed layer/substrate.

\* \* \* \* \*